United States Patent [19]

Blackstone

[11] Patent Number: 4,868,930
[45] Date of Patent: Sep. 26, 1989

[54] PROTECTIVE EYE WEAR

[76] Inventor: Joshua Blackstone, 614 Endicott St., Fort Collins, Colo. 80524

[21] Appl. No.: 185,776

[22] Filed: Apr. 25, 1988

[51] Int. Cl.⁴ ............................. A61F 9/00; A61F 9/04
[52] U.S. Cl. .............................................. 2/439; 2/15; 2/449; 2/454
[58] Field of Search ................... 2/10, 11, 12, 15, 435, 2/436, 437, 439, 443, 445, 448–449, 450, 453, 454

[56] References Cited

U.S. PATENT DOCUMENTS

| | | |
|---|---|---|
| 540,746 | 6/1895 | Lamb . |
| 1,562,319 | 11/1925 | Fairall ...................................... 2/454 |
| 2,208,336 | 7/1940 | Marciano ................................. 2/12 |
| 2,589,575 | 3/1952 | Richardson et al. .................... 2/454 |
| 2,614,255 | 10/1952 | Ellis ........................................... 2/12 |
| 2,679,191 | 5/1954 | Tomlin .................................. 2/453 X |
| 2,715,223 | 8/1955 | Stegeman . |
| 3,155,982 | 11/1964 | Baratelli .................................... 2/12 |
| 3,261,652 | 7/1966 | Magnus . |
| 3,384,903 | 5/1968 | Malcom, Jr. ......................... 2/12 X |
| 3,458,866 | 8/1969 | DeMan ...................................... 2/12 |
| 4,106,119 | 8/1978 | Taupin ....................................... 2/12 |
| 4,271,538 | 6/1981 | Montesi . |
| 4,610,036 | 9/1986 | LaPrairie ............................ 2/450 X |

FOREIGN PATENT DOCUMENTS

| | | | |
|---|---|---|---|
| 125726 | 10/1947 | Australia .................................. 2/24 |
| 78208 | 3/1951 | Norway ................................... 2/24 |

*Primary Examiner*—Werner H. Schroeder
*Assistant Examiner*—Jeanette E. Chapman
*Attorney, Agent, or Firm*—Dean P. Edmundson

[57] ABSTRACT

Protective eye wear is described which is useful as sunglasses, safety glasses, or the like. The product includes a unitary plastic lens piece or shield having a uniform thickness. The side edges of the lens piece are folded rearwardly to form side shields. A brow member is attached to the top edge of the lens piece and extends along the entire length of the lens piece and is perpendicular to the lens piece. Temple members can be attached to the ends of the lens piece or shield. The eye wear product can be made from plastic sheets.

21 Claims, 6 Drawing Sheets

PROTECTIVE EYE WEAR

FIELD OF THE INVENTION

This invention relates to protective eye wear such as sunglasses, safety glasses, and the like. In other aspect, this invention relates to methods and techniques for manufacturing sunglasses, safety glasses, and the like.

BACKGROUND OF THE INVENTION

Protective eye wear such as sunglasses and safety glasses have conventionally been made of glass and, more recently, of plastic. In most instances there are separate lens pieces, frame members, and temples. The lens pieces are secured in the frame members as individual items.

In some instances there have been provided sunglasses, safety glasses, and goggles having a single lens piece for covering both eyes. However, in some of these products there are separate frame members in which the lens piece must be secured or carried. In other of such products there is a frame integral with the lens piece, but these products must be injection molded using a liquid plastic. As a result, the frames are inherently thicker than the lens piece due to the nature of injection molding techniques.

This means that the optical clarity is different in the frame portion than it is in the lens portion of the eye wear. This accordingly limits the effective field of vision of the user. Also, no provision is made for adjustment of nose supports or pads. The thicker frames also add more weight to the product. The injection molding process is also rather expensive.

An eye shield or guard is described in U.S. Pat. No. 540,746 which includes two lens pieces (one for each eye) which are connected together by a flexible strip of cloth in the center above the nose. This two-piece construction is an inherently weak design which does not provide significant protection against frontal impact. Further, peripheral vision is impaired due to the presence of the connecting flexible strip.

Also, the back side of the eye shield of the patent is pulled against the skin of the wearer by an elastic cord and this is very cosmetically undesirable. Also, the edges of the shield may absorb sweat or other liquids, thereby rendering the contact with the face soggy and potentially irritating. Furthermore, the cushion at the edges of the shield impair peripheral vision. Also, the lack of temples is undesirable. The eye shield is not cosmetically appealing.

U.S. Pat. No. 1,562,319 describes goggles which are intended for stereoscopic viewing and are severely limited for use as safety eyewear or for cosmetic use. The face shield portion is made of two separate pieces which are adhered together in an overlapping manner with a cement. As a result the product does not provide significant protection against frontal impact. Indeed, the product is not suitable as safety wear; rather, it is intended for use in viewing stereoscopic motion pictures. The two lens pieces are planar (i.e., flat) and therefore would allow foreign materials to easily enter the eyes from either side or the bottom or the top. Because the lens pieces are flat and are overlapping in the center, there is much distortion inherent in the product. Further, there is no provision for nose pads or nose supports in the product. As a result, the product could not be worn for very long without discomfort or pain.

U.S. Pat. No. 2,715,223 describes a pair of goggles which are a molded plastic material. This molding is very expensive and complex due to tooling requirements and inherent limitations as to quantity of product which can be produced simultaneously. The molding process limits the manufacturing capability and does not readily enable decorative embellishment of the product. This product is not suitable for use as sunglasses. It requires use of a head strap to hold it in place. Further, the lens piece is a separate piece from the frame member.

U.S. Pat. No. 3,261,652 describes an adjustable length temple for use on sunglasses. The lenses are tinted but include horizontal elliptical slots. The entire product can be made as an integral unit by means of molding. This requires injecting heated liquid plastic into a mold where it cools. Due to limitations of the molding process, the thickness and the radii of the product are greater than desired. The cost and slow speed of manufacture are other disadvantages of the product. Also, molded products are inherently more difficult and expensive to provide with decorative embellishments, as they must be applied to each pair separately. Furthermore, lenses with slits or slots therein do not provide adequate protection from ultraviolet radiation, for example. The use of extra lenses over the slits result in a multi-piece construction which is subject to breakage, leaking (e.g., rain), and additional cost and complexity of manufacture.

U.S. Pat. No. 4,271,538 describes safety spectacles which are molded so as to provide a one piece front face piece. Due to inherent limitations of the molding process, the resulting product is heavier and more costly than desired. The molding process is inherently limited as to speed also because the heated plastic must cool before the product can be removed from the mold. Also, the number of pieces which can be formed at one time is limited to the number of molds which have been made.

Prior art wrap around or curved sunglasses and safety glasses may be categorized as: (1) those that are assembled from many separate parts (i.e., lenses, frames, side shields, brow shield, hinges, temples), (2) those that are molded using heated liquid plastic forced into a mold, (3) those that have two-piece face shields which are hinged or overlapping, and (4) those that have a rubbery frame which molds to facial curves. All of these types of products have inherent limitations and disadvantages.

Molded products are inherently limited in their ability to be provided with decorative embellishments. If any such embellishments are desired, they must be applied to the product in some manner after the product has been formed and then removed from the mold. This is expensive and also cumbersome. The molding process also makes the application and use of scratch-resistant coatings more expensive because such coatings must be applied to the product in an individual manner, thereby increasing labor and time requirements.

There has not heretofore been provided a protective eyewear product having the advantages of the present invention.

SUMMARY OF THE PRESENT INVENTION

In accordance with the present invention there is provided, in one embodiment a protective eye wear product or device which comprises:

(a) a unitary, optically clear plastic lens piece having a top edge, a lower edge, first and second side edges, and front and rear faces; wherein the side edges are folded rearwardly toward the rear face to form side shields; wherein the lens piece further comprises a brow member attached to the top edge of the lens piece, wherein the brow member includes first and second ends which are folded downwardly and secured to the side shields of the lens piece; and (b) first and second plastic temple members attached to the first and second side edges, respectively, of the lens piece.

The protective eye wear products of the invention are made of optically clear plastic of uniform thickness. The eye wear has a wider and safer field of view (i.e., excellent peripheral view) than exhibited by previous products.

The protective eye wear products can be provided as safety glasses or as sunglasses, as desired. The manufacture of the products can be performed simply, rapidly, and at relatively low cost. The manufacturing process used enables production of eye wear products from large sheets or rolls of plastic. No injection molding is required. Many units can be made simultaneously using the techniques of this invention.

Also, the plastic can be easily and readily provided with decorative embellishments, if desired, prior to manufacture of the products. Similarly, the plastic may be easily provided with a scratch-resistant coating prior to manufacture of the product. The coating is not affected during the manufacturing process, nor is the optical clarity of the plastic affected during manufacture of the products.

The protective eye wear products of this invention are cosmetically appealing (less bulky than prior art devices) and can be easily decorated, as desired, during the manufacture thereof. The products have fewer parts than prior art eye wear products, are light-weight and are very safe and durable. The products have very good strength to weight ratios. In the products of this invention the face shield or lens piece is braced and reinforced by the brow member and the side shields without need for heavy and thick cross-sections obtained from molding processes.

The temples can be hingably attached to the sides of the lens piece in many different manners. Also, the product includes integral nose support pads to facilitate comfort in wearing the eye wear product. The products of the invention also include vent areas at the top edge of the lens piece over the eyes. This prevents fogging of the lens piece by permitting escape of moisture from the lens areas.

Other advantages of the protective eye wear devices of this invention will become apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which:

FIGS. 13 and 14 are top views illustrating other types of hinge means which may be used in the protective eye wear products of this invention; and FIG. 15 is a side elevational, exploded view illustrating another type of temple member and lens piece of the invention.

DETAILED DESCRIPTION OF THE INVENTION

Figure 1:
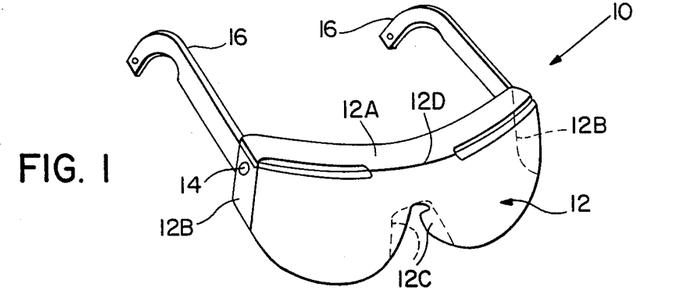
FIG. 1 is a front perspective view of one embodiment of protective eye wear product of the invention.
Figure 2:
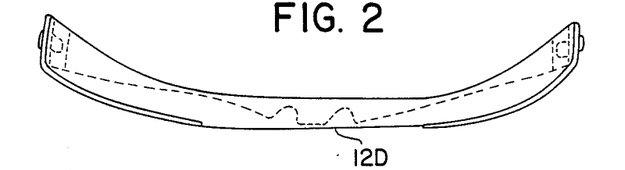
FIGS. 2A through 2D are top, front, side, and bottom views, respectively, of one embodiment of lens piece or face shield of the invention.
Figures 2B, 2C:
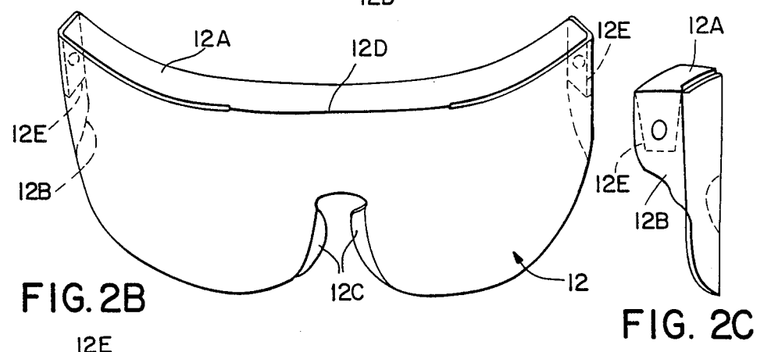
Figure 2D:
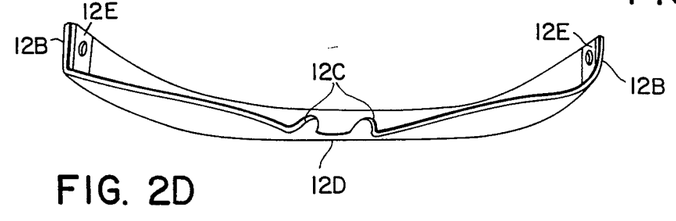

In FIG. 1 there is illustrated a preferred embodiment of protective eye wear device 10 of this invention. The device includes a unitary transparent, optically clear lens piece or face shield 12, brow piece, and side shields. The plastic has a uniform thickness and is optically clear throughout. Temple members 16 are secured to the insides of the side shields 12B.

Lens piece 12 includes a brow member 12A which extends along the top edge and which is perpendicular to the main body of the lens piece. Along line 12D the brow member 12A is integral with the main portion of the lens piece or face shield. This is also illustrated in FIGS. 2A through 2D which show the lens piece 12 without the temples attached.

The side edges 12B of the lens piece are folded rearwardly along fold line 12F, as illustrated, to form side shields. Temple members 16 are secured at their leading ends to the side edges of the lens piece and the ends of the brow member by means of a rivet or pin 14. Instead of a rivet it is possible to use an adhesive or plastic welding. Tabs or flanges 12C in the central lower portion of the lens piece form nose support or pad members. The nose bridge pads or supports are integral with the lens piece and may be folded as desired in order to adjust the width and position thereof. In this manner the lens piece can be adjusted to custom fit the nose by narrowing or widening the nose bridge fit and also to provide adjustment for where the lens piece rests or is supported on the nose, i.e., the eye wear can be adjusted closer or farther from the face, thereby providing adjustment for proper fit of the temples on the ears. The nose support pads are light in weight. Manual adjustment of the pads is simple.

The side shields 12B are formed by folding the side edges of the lens piece along fold lines 12F. The side shields are integral with the lens piece along the fold lines. The side shields provide reinforcement to the side edges of the lens piece and also provide protection for the eyes from foreign materials, light, and glare. In other words, the side shields are braces for the side edges of the lens piece to lend strength, rigidity and durability to the curved lens piece while at the same time providing protection against foreign materials and light.

The brow member or shield 12A is formed by folding the top edge of the lens piece along fold line 12D in a manner such that the brow member is perpendicular to the lens piece body. In other words, the brow member forms a 90° angle with the lens piece body along fold line 12D.

The brow member is integral with the lens piece along the fold line, but the remaining portions of the leading edge of the brow member beyond the fold line 12D are not integral with the top of the lens piece. This leaves long thin slots 12G between the top of the lens piece and the leading edge of the brow member. These slots serve as vents to allow air movement therethrough and thereby prevent moisture from fogging the inside of the lens piece in cold or humid environments. This significantly improves safety and function, allowing moisture to rise and escape from the eye wear across the eyes' field of vision.

The ends 12E of the brow member are folded downwardly and are secured to the side shields 12B, as illustrated in the drawings. The brow member serves as a brace to provide reinforcement to the lens piece. The leading edge of the brow member defines the curved lines for curvature of the lens piece, as illustrated in the drawings, to create a wrap-around effect.

The brow member or shield protects the eyes from foreign material, light, and glare entering the eye while acting as a continuous brace for the lens piece and the side shields 12B. This lends strength, rigidity, and durability to the curved lens piece in the top, face, and side planes.

The lens piece face shield may be manufactured in a range of desired sizes from, for example, 40 mm. by 100 mm. to 60 mm. by 175 mm. These size ranges can accommodate children and adults, with the nose bridge portion being sized accordingly.

The protective eye wear may be worn alone or over conventional eye glasses, as desired. An average adult size is about 55 mm. by 155 mm. for the lens piece.

The protective eye wear may be tinted or not, depending upon the intended use. When the plastic is tinted the eye wear provides protection from the sun and ultraviolet rays, thereby preventing eye strain and retinal damage. The amount of tinting may vary, as desired, and may be provided in accordance with conventional techniques.

The protective eye wear is also useful as safety glasses to provide protection from foreign materials entering the eyes from the front, top or sides. The eye wear also provides protection from frontal or side impact (e.g., in the case of falling or flying objects such as occurs in the operation of grinding wheels, wire wheels, polishing equipment, etc.).

The protective eye wear can also be made for use as welding glasses to provide protection from the glare of gas welding torches, with appropriate shielding tint. The eye wear also provides protection against flying sparks associated with welding processes.

The protective eye wear can also be provided as low cost, disposable, light duty protective wear for use, for example, by visitors and other persons who are temporarily exposed to potential eye hazards. The eye wear can easily be provided, during normal manufacture thereof, with decorative embellishment (e.g., to identify the company or person providing the eye wear).

The protective eye wear of the invention can also be provided as non-prescription eye wear, suitably decorated, for use as a dressing accessory to complement a wardrobe. For example, the eye wear may be provided in any desired color or combination of colors or designs.

The protective eye wear of this invention can be easily and inexpensively made from optical grade plastic sheet material. For example, in FIG. 3 there is illustrated a top view of a plastic sheet 20 in which a repeating pattern of lens piece precursors 30 have been cut. The sheet could be many times larger than illustrated and may have many more repeating patterns 30 cut therein, if desired. For example, the sheet could be several feet wide and several feet long, with hundreds of patterns of eye wear precursors per sheet.

Figure 3:
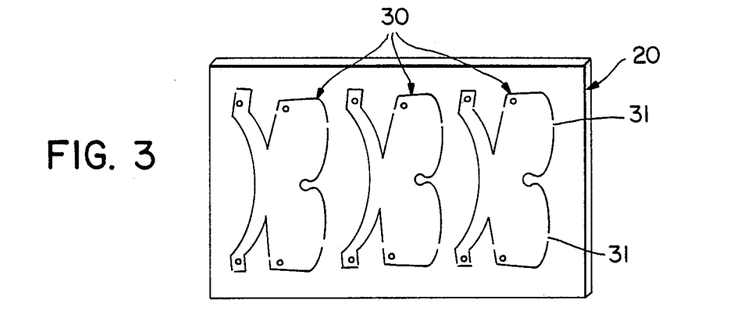
FIG. 3 is a top view illustrating a repeating pattern of precursors of lens pieces or face shields cut into a flat plastic sheet.

The patterns 30 are preferably cut by means of a die (or a plurality of dies, if desired) in a manner such that the cut lines are discontinuous. This leaves small areas 31 which have not been cut through. As a result, the lens piece precursor remains in the plane of the sheet 20 and is carried thereby.

Figure 4:
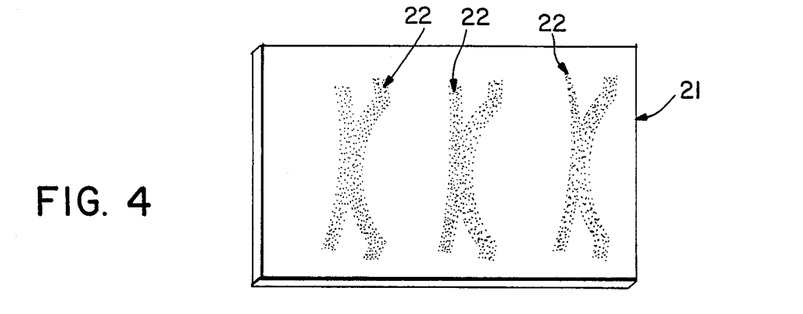
FIG. 4 is a top view of a plastic sheet having a repetitive decorative pattern coated or printed thereon.
Figure 4A:
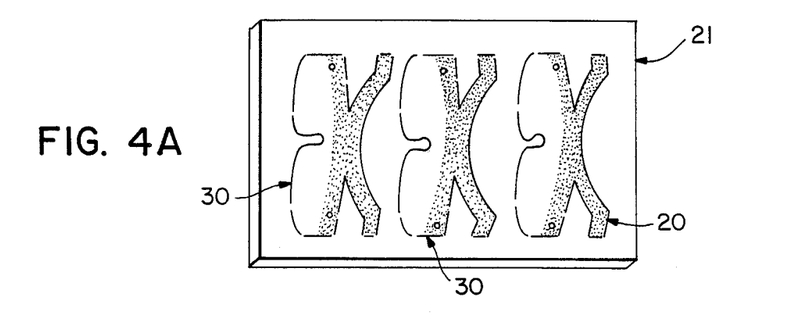
FIG. 4A is a top view of the plastic sheet shown in FIG. 4 after it has been die cut to provide a repeating pattern of precursors of lens pieces or face shields in the plastic sheet.
Figure 4B:
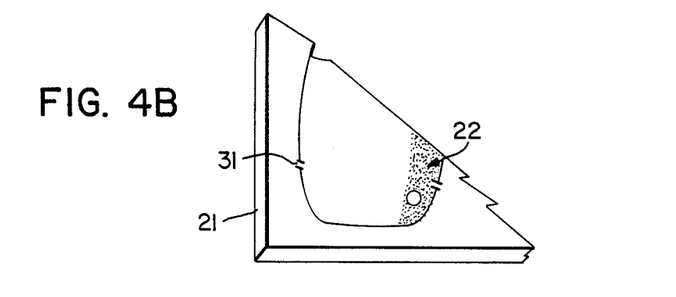
FIG. 4B is an enlarged fragmentary top view of a portion of the sheet shown in FIG. 4A.
Figure 4C:
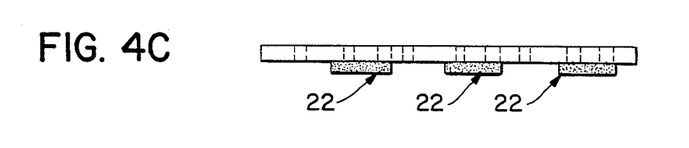
FIG. 4C is an edge view of the sheet shown in FIG. 4A.

FIGS. 4 through 4C illustrate another variation and capability of the present invention. In FIG. 4 the sheet 21 has been coated or printed in a repetitive pattern 22 with a layer of colored material which is of a different color or tint than the sheet 21. For example, the pattern 22 may be provided by conventional silk screening techniques or any other desired means. The pattern 22 may be provided in order to simulate a frame for the finished eye wear product, for example.

When the sheet material 21 is cut with pattern 30 (as illustrated in FIGS. 4A and 4B), layer 22 is located along the upper edges of the front portion of the lens piece and over the entire brow member.

Any other desired pattern for layer 22 may be used, as necessary or desired. The color and the thickness of layer 22 may also vary. In the edge view of FIG. 4C the layer 22 is shown to be very thick but this is not to scale. The layer 22 is shown as being very thick only for illustrative purposes. The layer 22 may simulate the appearance of separate structural frame members, for example.

The processes of printing or silk-screening decorative embellishment onto the plastic sheet are conventional and are an inexpensive means of applying colors, patterns, and words. These methods are essentially limited to application on flat stock material.

Because prior art protective eye wear is either injection molded plastic or is assembled from multiple small parts which have been molded, cast, or machined, prior art eye wear cannot simply or inexpensively accept complex external decoration on multiple pairs of eye wear simultaneously. On the other hand, in the present invention, flat sheets of plastic can be easily, rapidly, and efficiently printed or silk-screened with multiple colors and in any desired design.

Figure 5:
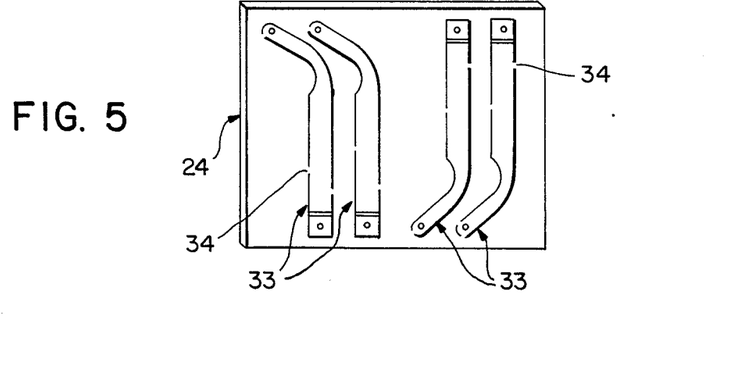
FIG. 5 is a top view of a plastic sheet having a repeating pattern of temple members or bow members cut into the sheet.
Figure 5A:
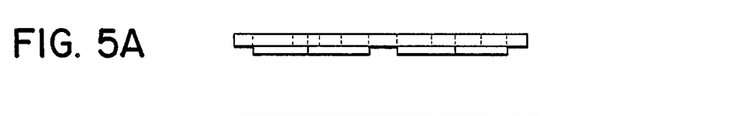

FIG. 5 is a top view of a plastic sheet 24 in which a repeating pattern 33 has been cut to form temple precursors. The cut lines are discontinuous so that small areas 34 of the sheet remain in order to keep the temple precursors within the sheet. If desired, the temples could be completely cut through and separated from the sheet 24 in one step. Alternatively, they may be cut from the sheet in a later step.

Figures 10, 11:
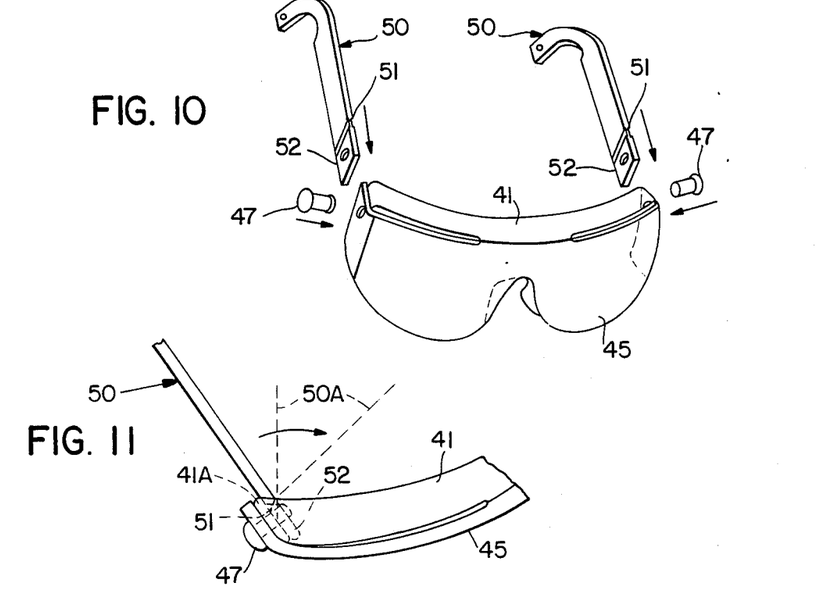
FIG. 10 is a perspective exploded view illustrating the manner in which the temple members are secured to the side edges of the lens piece shown in FIG. 9A.
FIG. 11 is a top fragmentary view illustrating the manner in which a preferred type of temple member is secured to the side edge of the lens piece.
Figure 12A:
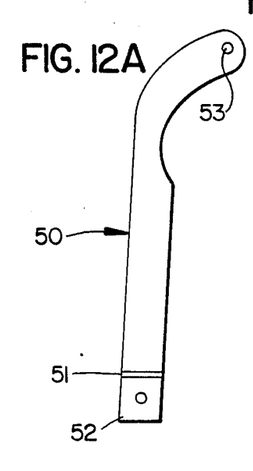
FIGS. 12A and B are side and edge views, respectively, of a preferred type of temple member used in this invention.
Figures 12B, 13, 14:
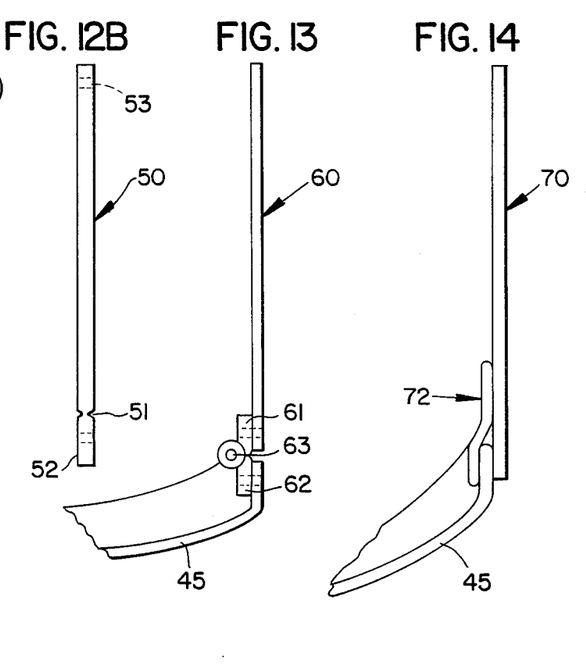

Preferably the temples include an integral living hinge. For example, as shown in FIG. 5, the temple can be embossed to provide an indentation 36 in the form of a line transversely of the temple member near the forward end. The indentation may be provided from both the top and bottom surfaces of the plastic (e.g., about ⅜ inch from the end of the temple). The indentation enables the temple to fold on the line without breaking. The forward end of the temple is secured to a side edge of the lens piece as illustrated in FIGS. 11 and 12. This is a living hinge.

The embossing to provide indentation line 36 is done simultaneously with the die cutting to form the temple precursors. This makes it possible to produce many temples and hinges each time the die is struck.

Figure 6:
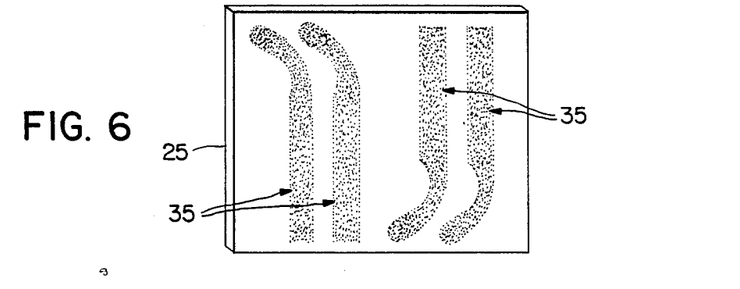
FIG. 6 is a top view of a plastic sheet having a repeating decorative pattern coated or printed thereon.
Figure 6A:
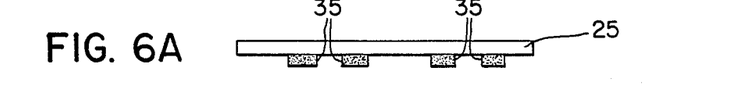
FIG. 6A is an edge view of the plastic sheet shown in FIG. 6.

FIGS. 6 and 6A are top and edge views, respectively, illustrating another variation of the invention. Plastic sheet 25 has been coated or printed on its upper surface with a repeating pattern 35, as illustrated. The pattern corresponds generally to the shape of the temple members to be cut from the sheet 25.

Figures 7, 7A:
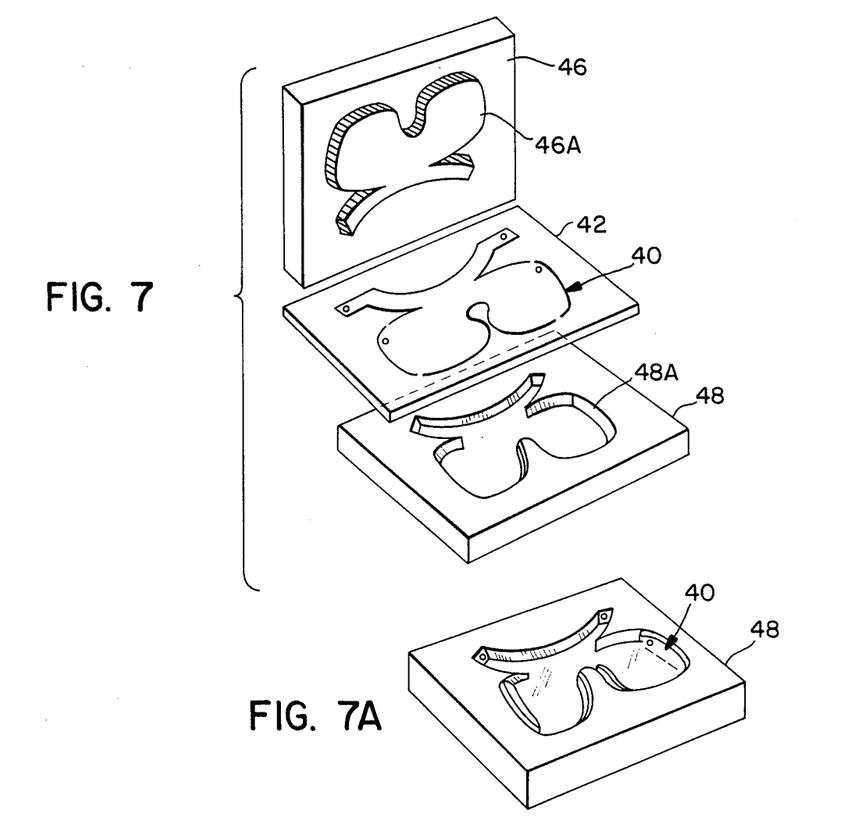
FIG. 7 is a perspective view illustrating one manner in which a lens piece or face shield precursor is separated from a plastic sheet by the use of male and female dies.
FIG. 7A is a perspective view showing the eye wear precursor in the female die after separation from the plastic sheet.
Figure 7B:
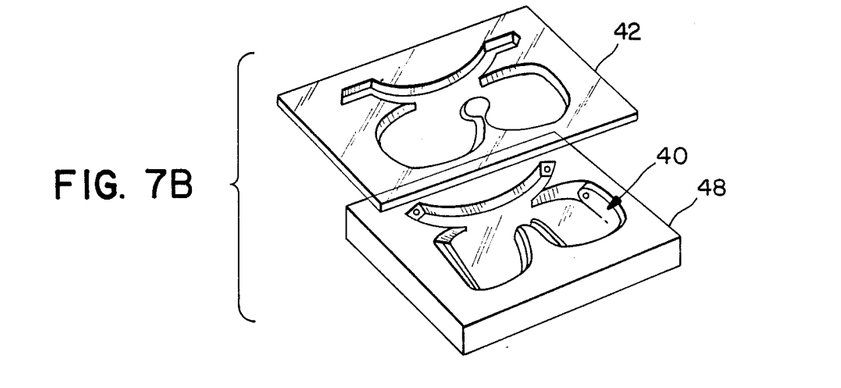
FIG. 7B shows the eye wear precursor in the die and the plastic sheet from which the precursor was separated.

FIGS. 7, 7A and 7B illustrate one manner in which a lens piece precursor 40 is separated from a plastic sheet 42 using male folding die 46 and female folding die 48. The sheet 42 is placed between the two dies, after which the dies are urged together. Die 46 includes a projecting portion 46A while die 48 includes a recess 48A therein. When the projecting portion of die 46 forces the precursor 40 into the recess in die 48, the ends of the brow member are folded rearwardly as are the side edges of the lens piece and the nose support portions.

Using polycarbonate plastic material it is not necessary to use heat in the folding process to adequately crease and fold the brow shield and side shields. However, when using plastic which is thicker than about 0.040 inch, or when the speed of the die folding process is increased significantly and dwell time in the die is decreased, the male die may be heated along the fold lines to facilitate folding. For example, the male die may be heated to about 100° to 300° F. in the desired areas by means of electrical resistance heating, depending upon the plastic composition, plastic thickness, and speed of operation. If desired, it is also possible to pre-warm the plastic sheet stock in an oven or with heat lamps to achieve the same goal as heating the male die.

Figure 8:
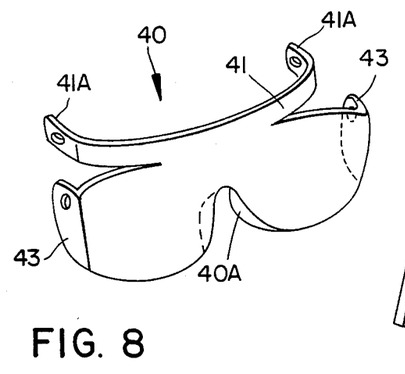
FIG. 8 is a perspective view showing the eye wear precursor after being removed from the female die.
Figure 8A:
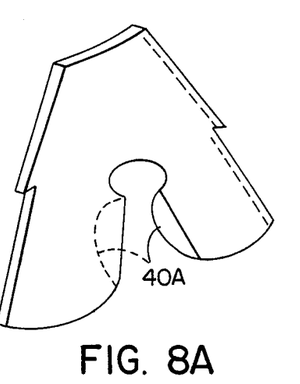
FIG. 8A is an enlarged perspective fragmentary view of a portion of the eye wear precursor shown in FIG. 8.

FIG. 8 illustrates the eye wear precursor 40 after it has been removed from the recess in mold 48. The ends 41A of the brow member 41 have been folded rearwardly as have the ends 43 of the lens piece. The nose support tabs 40A are also folded rearwardly. This is also illustrated in the fragmentary view shown in FIG. 8A.

Figure 9:
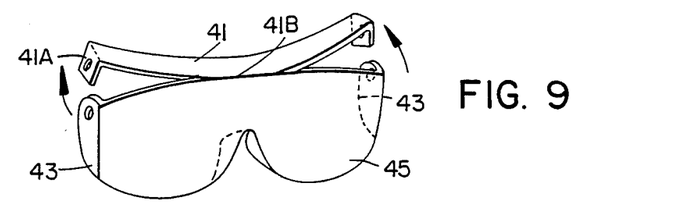
FIG. 9 is a perspective view illustrating the manner in which the eye wear precursor of FIG. 8 is shaped and folded.

FIG. 9 illustrates the manner in which the brow member 41 is folded along line 41B such that the brow member is perpendicular to the lens piece or face shield 45. Then the ends 43 of the lens piece are urged rearwardly in the direction of the arrows to obtain the shape shown in FIG. 9A. This provides curvature to the lens piece at each end.

Figure 9A:
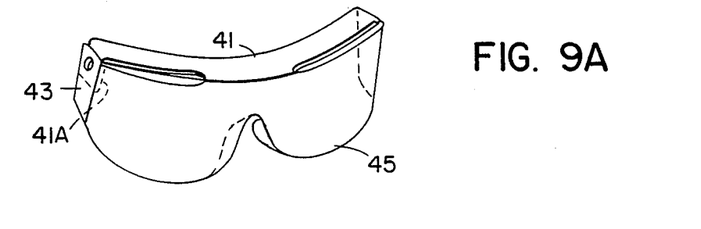
FIG. 9A is a perspective view illustrating the eye wear after it has been shaped and folded.

This curvature serves to put the lens the same distance from the pupil across the arc of the field of view, thereby preventing optical distortion. Also, because the lens piece wraps around the eyes a wider unobstructed field of view is provided. Further, the curved lens piece protects the eyes from foreign material entering from the side of the eye wear.

The apertures in ends 43 of the lens piece and the apertures in the ends 41A of the brow member are intended to register when the lens piece is curved rearwardly at the ends.

In FIGS. 10 and 11 there is illustrated the manner in which temple members 50 are secured at their leading ends 52 to the side shields of the lens piece 45. Pin or rivet 47 is inserted through the registering apertures. Alternatively, adhesives or welding may be used to joint these parts together.

Each temple member includes a hinge 51 near its leading end. In the embodiment shown in FIGS. 10 and 11, the hinge 51 comprises an area of reduced thickness in the temple member. This type of hinge is also illustrated in FIGS. 12A and B.

As explained above, the area of reduced thickness is a line near the forward end of the temple which is embossed into the flat plastic sheet at the same time that the temple piece is die cut in the plastic. This die cutting and embossing can be performed in multiples of many hundred per second.

Each temple member 50 can pivot inwardly in the direction of the arrow shown in FIG. 11 (as illustrated by dotted lines 50A, for example). It may pivot inwardly to any position desired. However, the temple member is prevented from pivoting outwardly (beyond perpendicular to the plane of the lens piece) by means of the rear portion of end 41A of brow member 41. No wire reinforcement or thick casting is required. Also, no moving parts are required, nor are there any separate parts to be broken or lost.

The aperture 53 at the rear end of the temple member is for the purpose of facilitating attachment thereto of a safety strap, for example.

FIGS. 13 and 14 are top views illustrating two other types of hinges which are useful in the protective eye wear products of this invention. Thus, in FIG. 13 there is illustrated a temple member 60 pivotably secured to lens piece 45 by means of a conventional hinge member comprising arms 61 and 62 which are pivotably connected by means of pin 63. One arm 61 is secured to the leading end of temple 60 and the arm 62 is secured to the end of the lens piece, as shown.

FIG. 14 shows a temple 70 which is pivotably connected to the end of lens piece 45 by means of a flexible strip or member 72. One end of strip 72 is adhesively secured to the leading end of temple 70 and the other end of the strip is adhesively secured to lens piece 45. This hinge permits the temple to fold or pivot inwardly toward the rear of the lens piece but it prevents the temple from folding outwardly beyond the position shown. Any permanently flexible, durable material may be used for strip 72. Adhesive coated vinyl or polyester as well as fabric tape may be used, for example. The strip may be reinforced or not, as desired. As one example there may be used a polyvinylchloride strip (about 0.010 to 0.020 inch thick) which may be glued or riveted to the temples and the side shields.

In FIG. 15 there is illustrated another variation of the protective eye wear product of the invention. Thus, there is shown a side elevational view of another embodiment of eye wear 80 having a long or deep side shield 82 which extends to the bottom of the lens piece. The end 84A of brow shield 84 extends downwardly along the inside of the side shield 82.

The temple member 85 includes forward end 86 and embossed hinge line 87 parallel to the forward end of the temple. The forward end of the temple extends downwardly the same distance as the side shield 82 so that when the temple is secured to the side shield there is provided very good protection of the eyes from foreign materials.

The one-piece integral hinges shown herein are very advantageous in protective eye wear for several reasons. These hinges are easy to make by simply embossing the plastic. This is also more economical than using a conventional hinge. Furthermore, the one-piece hinge is shatterproof and therefore is safer than previous types of hinges used in eye wear.

Polycarbonate is the preferred plastic for use in making the eye wear products of this invention. The thickness may be selected as desired. Other types of optical grade plastic may also be used (e.g., commercially available plastic such as CR-39). The temple members are preferably made of nylon or polyethylene, etc. which are durable and resilient and therefore are advantageous for flexing without breaking in the integral hinge embodiment.

The plastic is preferably coated with a conventional scratch-resistant coating. The plastic is very easily coated while in sheet form using conventional coating and processing equipment. In this manner all portions of the eye wear product can be coated with scratch-resistant coating (not just the lens piece). The plastic sheet material can also be easily and efficiently printed or silk-screened with any desired color or design. Then the plastic sheet can be die cut to produce the eye wear precursors in many replications per sheet. Since all portions of the eye wear products are produced from optical grade plastic, the resulting product provides much better peripheral vision than previous products.

The eye wear products of the invention can also be produced efficiently from plastic roll goods as well as from plastic sheets. Thus, the techniques of this invention can be used to produce protective eye wear in a continuous process using rotary dies. This is a very cost efficient manner of producing protective eye wear products.

As another variation, instead of printing or silk-screening a colored pattern onto the flat plastic sheet, hot foil stamping and embossing techniques may be used to create metallic embellishment and raised embossed decoration and structural ridges simultaneously with the folding process. This eliminates separate embellishment processes or special pre-coloration of raw stock, thereby reducing labor and material costs.

The protective eye wear of the invention is very durable due to the presence of a brow shield and side shields to brace and reinforce the product, while minimizing the weight.

The thickness of the plastic used to make the eye wear products of the invention may vary considerably, as desired. For example, one may use plastic sheets as thin as about 0.020 inch or as thick as about 0.120 inch, if desired.

Although reference is made herein to the products of the invention being "protective" eye wear, it is to be understood that the eye wear products of this invention may also be made primarily for use as cosmetic eye wear. Thus, reference herein to protective eye wear also includes reference to cosmetic eye wear.

Other variants are possible without departing from the scope of the present invention.

What is claimed is:

1. Protective eye wear comprising:
   (a) a unitary, optically clear plastic lens piece having a top edge, a lower edge, first and second side edges, and front and rear faces; wherein said side edges are folded rearwardly toward said rear face to form side shields; wherein said lens piece further comprises a brow member attached to said top edge of said lens piece, wherein said brow member includes first and second ends and a central portion therebetween; wherein said first and second ends are folded downwardly and secured to said side shields of said lens piece; wherein said top edge of said lens piece is integral with said central portion of said brow member; wherein first and second slots are defined between said first and second ends of said brow member and said top edge of said lens piece; and
   (b) first and second temple members attached to said first and second side edges, respectively, of said lens piece.

2. Eye wear in accordance with claim 1, wherein said lens piece, brow member, and side shields have a uniform thickness.

3. Eye wear in accordance with claim 1, wherein said brow member is perpendicular to said lens piece.

4. Eye wear in accordance with claim 1, wherein said plastic lens piece is tinted.

5. Eye wear in accordance with claim 1, wherein said lower edge of said lens piece includes integral adjustable nose support pads.

6. Eye wear in accordance with claim 1, wherein said front face of said lens piece includes a simulated frame pattern thereon.

7. Eye wear in accordance with claim 6, wherein said simulated frame pattern comprises an ink pattern having a color differing from the color of said lens piece.

8. Eye wear in accordance with claim 1, wherein said temple members have uniform thickness.

9. Eye wear in accordance with claim 1, wherein each said temple member includes an integral hinge portion.

10. Eye wear in accordance with claim 9, wherein said hinge portion comprises an area of reduced thickness to facilitate pivoting.

11. Eye wear in accordance with claim 9, wherein said hinge portion comprises a flexible strip having first and second ends, wherein said first end is adhesively secured to said temple member and said second end is adhesively secured to a said side edge of said lens piece.

12. Eye wear in accordance with claim 2, wherein said lens piece has a thickness in the range of about 0.02 to 0.1 inch.

13. A protective eye wear shield comprising a unitary, optically clear plastic lens piece having a top edge, a lower edge, first and second side edges, and front and rear faces; wherein said side edges are folded rearwardly toward said rear face to form side shields; wherein said lens piece further comprises a brow member attached to said top edge of said lens piece, wherein said brow member includes first and second ends and a central portion therebetween; wherein said first and second ends are folded downwardly and secured to said side shields of said lens piece; wherein said top edge of said lens piece is integral with said central portion of said brow member; wherein first and second slots are defined between said first and second ends of said brow member and said top edge of said lens piece.

14. A shield in accordance with claim 13, wherein said lens piece has a uniform thickness.

15. A process for making a unitary protective eye wear lens piece comprising the steps of:
 (a) providing a flat, optically clear plastic sheet;
 (b) cutting a pattern in said sheet corresponding to a lens precursor having an integral lens portion having a top edge, first and second side edges, and front and rear faces; wherein said precursor further includes a brow member having first and second ends and a central portion therebetween; wherein said top edge of said lens portion is integral with said central portion; wherein said pattern is created by a die which cuts around the periphery of said lens portion and said brow member;
 (c) separating said precursor from said sheet; and
 (d) shaping said lens precursor in a manner such that said side edges are folded rearwardly toward said rear face to form side shields, wherein said brow member is folded rearwardly and said first and second ends of said brow member are folded downwardly and secured to said side shields of said lens portion; and wherein first and second slots are defined between said first and second ends of said brow member and said top edge of said lens piece.

16. A process in accordance with claim 15, wherein said plastic sheet is provided in roll form.

17. A process in accordance with claim 15, wherein said pattern is created by a die which provides a discontinuous cut.

18. A process in accordance with claim 17, wherein said precursor is separated from said sheet by placing said sheet between male and female dies and urging said dies together.

19. A process in accordance with claim 16, wherein said pattern in said sheet is provided by a rotary die.

20. A process in accordance with claim 15, wherein said sheet is coated with a colored pattern simulating a frame for said lens piece.

21. A process in accordance with claim 15, wherein said lens portion includes integral nose support pads.

* * * * *